(12) United States Patent
Visser et al.

(10) Patent No.: US 11,703,503 B2
(45) Date of Patent: Jul. 18, 2023

(54) BIOSENSOR BASED ON CAPTURE MOLECULES WITH DIFFERENT AFFINITIES

(71) Applicant: Technische Universiteit Eindhoven, Eindhoven (NL)

(72) Inventors: Emilius Willem Adriaan Visser, Eindhoven (NL); Leonardus Josephus van Ijzendoorn, Eindhoven (NL); Menno Willem José Prins, Rosmalen (NL)

(73) Assignee: Technische Universiteit Eindhoven, Eindhoven (NL)

( * ) Notice: Subject to any disclaimer, the term of this patent is extended or adjusted under 35 U.S.C. 154(b) by 917 days.

(21) Appl. No.: 16/471,113

(22) PCT Filed: Jan. 2, 2018

(86) PCT No.: PCT/EP2018/050019
§ 371 (c)(1),
(2) Date: Jun. 19, 2019

(87) PCT Pub. No.: WO2018/122401
PCT Pub. Date: Jul. 5, 2018

(65) Prior Publication Data
US 2020/0025751 A1 Jan. 23, 2020

Related U.S. Application Data

(60) Provisional application No. 62/439,833, filed on Dec. 28, 2016.

(51) Int. Cl.
*G01N 33/53* (2006.01)
*G01N 33/543* (2006.01)
*G01N 21/63* (2006.01)
*G01N 33/542* (2006.01)
*G01N 33/557* (2006.01)

(52) U.S. Cl.
CPC ........... *G01N 33/543* (2013.01); *G01N 21/63* (2013.01); *G01N 33/542* (2013.01); *G01N 33/557* (2013.01)

(58) Field of Classification Search
None
See application file for complete search history.

(56) References Cited

U.S. PATENT DOCUMENTS

2019/0194345 A1* 6/2019 Herr .................... A61K 39/295

FOREIGN PATENT DOCUMENTS

| WO | WO2015120147 | 8/2015 |
|---|---|---|
| WO | WO2015195404 | 12/2015 |
| WO | WO2015195494 | 12/2015 |

OTHER PUBLICATIONS

Scheepers. Time-dependent tethered particle motion for measuring dissociation kinetics of short complementary DNA oligonucleotides. Jan. 2016. https://www.semanticscholar.org/paper/Time-dependent-tethered-particle-motion-for-of-DNA-Scheepers/9b5c18b10ff98c1cf0aac00946d61b3db981c7f1.
Brinkers et al. Single Molecule Detection of Tuberculosis Nucleic Acid Using Dark Field Tethered Particle Motion. IEEE Symposium on Biomed. Imaging, 2010, 1269-1272.
Plenat et al. High-througput single molecule analysis of DNA-protein interactions by thethered particle motion. Nucleic Acids Research, 2012 40(12) 8 pages.

* cited by examiner

*Primary Examiner* — Gary Counts
(74) *Attorney, Agent, or Firm* — Casimir Jones, S.C.; Tanya A. Arenson

(57) ABSTRACT

Provided herein is a method for biosensing a target substance [110] using a collection of particles [104] tethered to a surface [100] by tether molecules [102] and a plurality of capture molecules. A concentration of the target substance is determined from the time sequence of individual association/dissociation rates of the capture molecules. Competitive assay configurations are also described.

7 Claims, 3 Drawing Sheets

Fig. 4A     Fig. 4B
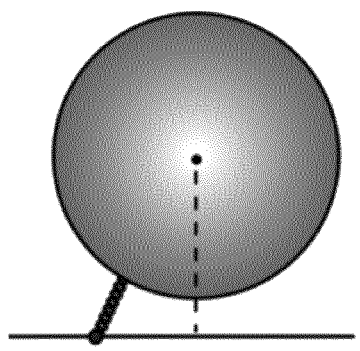 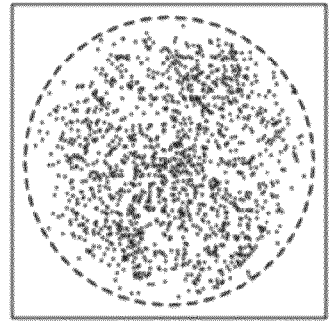
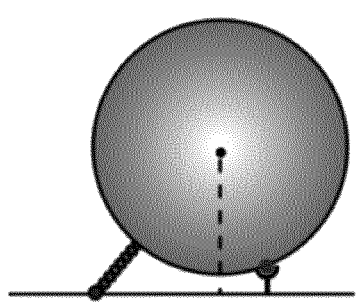 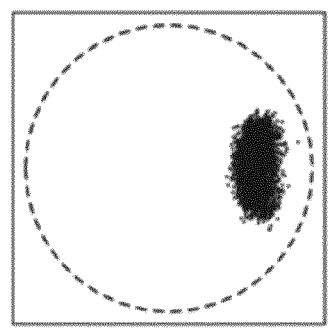
Fig. 4C     Fig. 4D
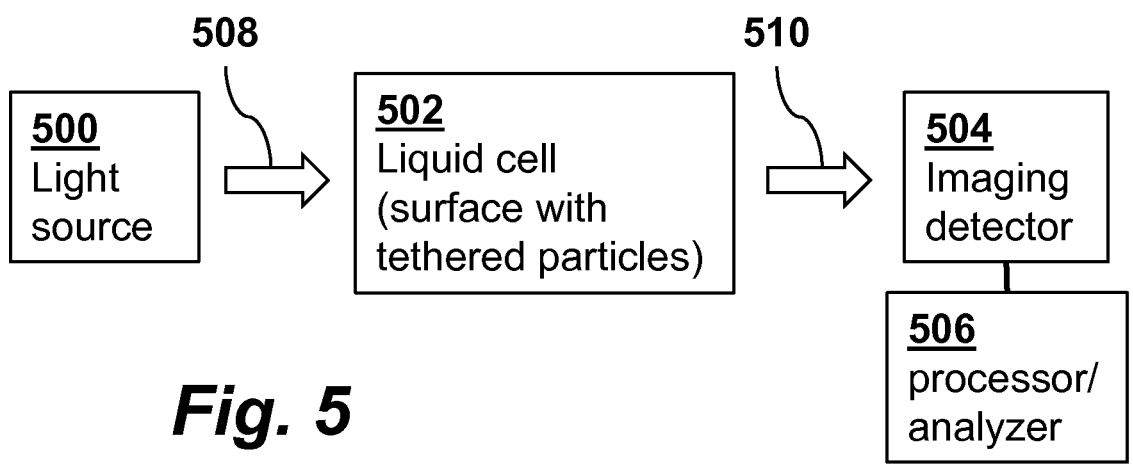
*Fig. 5*

BIOSENSOR BASED ON CAPTURE MOLECULES WITH DIFFERENT AFFINITIES

CROSS-REFERENCE TO RELATED APPLICATIONS

This application is a 371 of PCT application PCT/EP2018/050019 filed Jan. 2, 2018. PCT application PCT/EP2018/050019 claims the benefit of U.S. Provisional application 62/439,833 filed Dec. 28, 2016.

FIELD OF THE INVENTION

The present invention relates generally to biosensors for detecting target substances. More specifically, it relates to techniques for detecting target substances using biosensors where the presence of the target substance is derived from measurements of tethered particle motion (TPM).

BACKGROUND OF THE INVENTION

Tethered particle biosensing is a known technique for detecting the concentration of target substances. It has application to biochemical sensing, continuous monitoring, biochemical patient monitoring and body biomolecular monitoring. For example, WO/2016/096901 describes a biosensor based on a tethered particle, and methods for sensing the concentration of a target substance by measuring tethered particle motion. Specifically, in this tethered-particle biosensor, a microscale or nanoscale particle is tethered to a substrate by a tether molecule. In a sandwich assay, the particle and substrate are functionalized with capture molecules, both of which can bind to the target substance. When no target substance is present, the particle moves freely on its tether. In the presence of the target substance, however, the target substance binds to both capture molecules, constraining the motion of tethered particle.

The motion of the tethered particle is typically measured optically using a light source to illuminate a liquid cell containing a multitude of particles tethered to a surface within the cell. Various microscopy imaging techniques may be used such as bright field illumination, dark field illumination, evanescent wave illumination, absorption detection, scattering detection, fluorescence detection, etc. An imaging detector produces series of images of the tethered particles, and a processor analyzes the images to determine spatial coordinate parameters over time that are representative of the state of tethered particle motion within the cell.

The presence of the target molecule in the cell is detected by determining from the spatial coordinate parameters whether the tethered particle motion corresponds to an unbound state or a more restricted bound state. To empirically discriminate these states from each other, the bound state needs to have a sufficiently long lifetime, i.e., both capture molecules should have a sufficiently low dissociation rate. In addition, for high sensitivity to the presence of the target substance, the bound state should be quickly formed in the presence of the target substance, i.e., both capture molecules should have a sufficiently high association rate.

SUMMARY OF THE INVENTION

In contrast with known tethered particle biosensing techniques, embodiments of the present invention are based on the use of two capture molecules with unequal dissociation rates. Preferably, the dissociation rates of the two capture molecules differ by a factor of three or more. As a result of this difference, conventional wisdom would expect that the sub-optimal dissociation rate of one capture molecule will shorten the lifetime of the bound state and thereby adversely affect the ability to discriminate the bound and unbound states of the particle motion. However, the inventors have discovered that the use of two capture molecules with dissociation rates that differ by a factor of three or more can still provide adequate distinguishability while providing an added benefit of enhancing the switching rates and providing an over-all improved biosensing system. For example, enhanced switching rates provide improved detectability, signal to noise ratio, calibration, statistics, discrimination capability, sensitivity and/or specificity.

In one aspect, the invention provides a method for biosensing a target substance. The method includes bringing a matrix containing the target substance into contact with a sensor device having a surface, a collection of particles tethered to the surface by tether molecules, and a collection of capture molecules, where the collection of capture molecules comprises first capture molecules attached to the particles or to the tether molecules, and second capture molecules attached to the surface or to the tether molecules, where the first capture molecules are selected to bind to the target substance and have a first target dissociation rate, and the second capture molecules are selected to bind to the target substance and have a second target dissociation rate that differs from the first target dissociation rate by at least a factor of three.

The method also includes detecting a time series of a spatial coordinate parameter of the particles, where the spatial coordinate parameter is measured relative to the surface, and identifying within the detected time series a time sequence of individual association/dissociation events of the target substance with the capture molecules, where each of the events corresponds to a change between binding states of a first capture molecule CM1 and a second capture molecule CM2 to a target substance T. The method also includes determining a concentration of the target substance in the matrix from the identified time sequence of individual association/dissociation events.

In some embodiments, the change between binding states is a change between a sandwich-like state with T bound to both CM1 and CM2 and an open state with T not bound to CM1, T not bound to CM2 or T not bound to both CM1 and CM2.

In some embodiments, determining a concentration of the target substance from the detected time sequence of individual association/dissociation events comprises determining characteristic times of reactions of the capture molecules with the target substance.

In some embodiments, determining a concentration of the target substance from the detected time sequence of individual association/dissociation events comprises analyzing the spatial coordinate parameter and a second moment divergence of the spatial coordinate parameter.

In some embodiments, detecting a time sequence of individual association/dissociation events of the target substance with the capture molecules comprises measuring multiple spatial coordinate parameters of the particles and second moment divergences of the multiple spatial coordinate parameters of the particles.

In some embodiments, determining a concentration of the target substance from the detected time sequence of individual association/dissociation events comprises analyzing the measured spatial coordinate parameter and/or its time derivative with a second moment divergence function to determine the significance of an observed deviation in a data channel and to determine the divergence time point at which the behavior of the particle has changed, through back-extrapolation of the second moment divergence function.

In some embodiments, determining a concentration of the target substance from the detected time sequence of individual association/dissociation events comprises determining a duration of target substance capture states or an average occupancy of the capture molecules by the target substance.

In another aspect, the invention provides a method for biosensing a target substance. The method includes bringing a matrix containing the target substance into contact with a sensor device having a surface, a collection of particles tethered to the surface by tether molecules, a collection of target-analogues, and a collection of capture molecules, where the collection of capture molecules are attached to the particles or to the surface, and wherein the collection of target-analogues is attached to the particles or to the surface, where the capture molecules are selected to bind to the target substance and have a target dissociation rate, and the target-analogues are selected to bind to the capture molecules and have a target-analogue dissociation rate that differs from the target dissociation rate by at least a factor of three. The method also includes detecting a time series of a spatial coordinate parameter of the particles, wherein the spatial coordinate parameter is measured relative to the surface, and identifying within the detected time series a time sequence of individual association/dissociation events of the target substance with the capture molecules, where each of the events corresponds to a change between binding states of a capture molecule to a target substance or to a target-analogue. The method also includes determining a concentration of the target substance in the matrix from the identified time sequence of individual association/dissociation events.

In another aspect, the invention provides a biosensing device for detecting a target substance. The device includes a cell comprising on its interior a biosensing surface; a light source that emits light into the cell; a light detector that senses light from the cell; and a processor that determines concentration of the target substance in the cell from sensed light from the cell. The biosensing surface has a surface, a collection of particles tethered to the surface by tether molecules, and a collection of capture molecules. The collection of capture molecules comprises first capture molecules bound to the particles or to the tether molecules, and second capture molecules bound to the surface or to the tether molecules. The first capture molecules are selected to bind to the target substance and have a first target dissociation rate, and the second capture molecules are selected to bind to the target substance and have a second target dissociation rate that differs from the first target dissociation rate by at least a factor of three. The processor detects a time series of a spatial coordinate parameter of the particles, and identifies within the detected time series a time sequence of individual association/dissociation events of the target substance with the capture molecules, and determines the concentration from the identified time sequence of individual association/dissociation events, where each of the events corresponds to a change between binding states of a first capture molecule and a second capture molecule to a target substance.

BRIEF DESCRIPTION OF THE DRAWINGS

FIG. 4A and FIG. 4C illustrates a tethered particle in an unbound state and a bound state where its motion is restricted, respectively, according to an embodiment of the invention. FIG. 4B and FIG. 4D illustrate measured x-y coordinate positions of the unbound particle over time in unbound and bound states, respectively, according to an embodiment of the invention.

FIG. 5 is a schematic diagram of an optical biosensing device for implementing tethered particle biosensing according to an embodiment of the invention.

DETAILED DESCRIPTION

Figure 1A:
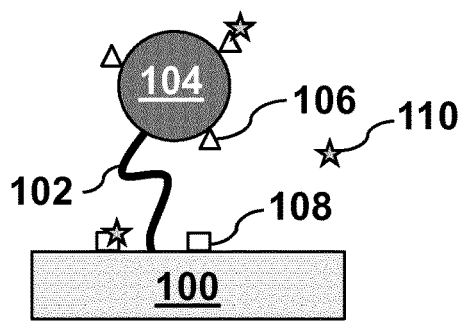
FIG. 1A and FIG. 1B are schematic diagrams illustrating a tethered particle biosensing configuration in an unbound state and bound state, where the particle and substrate are functionalized with capture molecules, according to an embodiment of the invention.

In the field of biosensing, it is generally known that low-concentration target substances can sensitively and specifically be measured in a sandwich assay, using two or more capture molecules. The target substance that one wants to measure may consist of a molecule or more than one molecule, e.g., a molecular complex, a multimer, a virus or a virus fragment, a microbe or a microbe fragment, a cell fragment, a vesicle, or a liposome. The target, also called an analyte, can be a surrogate for a substance that one wants to quantify.

Typically, capture molecules are used which have affinities that are as high as possible, i.e., capture molecules with dissociation rates that are as low as possible (low $k_{off}$), so which have slow unbinding characteristics (long lifetime, large $\tau_{off}$).

It is also generally known that targets can sensitively and specifically be measured in a competition assay, using two or more capture molecules, of which at least one is a target-analogue or a competitor molecule. Again, for the detection of low target concentrations, typically capture molecules are used which have affinities that are as high as possible, i.e. capture molecules with dissociation rates that are as low as possible (low $k_{off}$), so which have slow unbinding characteristics (long lifetime, large $\tau_{off}$).

In a biosensor with single-molecule resolution, the measurement of target concentration relates to a number or a rate of detected binding and/or unbinding events. In such a biosensor, it is advantageous to have good statistics, i.e. to measure a high number of binding and unbinding events in a given time, for good signal and data analysis, high sensitivity, accuracy, specificity, robustness, etc. This requires that lifetimes of individual signal events are not too long, otherwise insufficient events are recorded in a given measurement timespan.

In the case of a TPM biosensor, it can be advantageous if the state in which the tethered particle motion is restricted is short-lived. The state lifetime should be long enough for it to be detectable, but otherwise it is advantageous if it is short-lived, because that enhances the statistics.

On the other hand, it can be advantageous if target molecules are already detectable at low target concentration in the matrix. This requires at least one capture molecule in the TPM system (e.g. on the particle, on the substrate, or attached to the tether) that generates a long lifetime when bound to a target molecule.

Embodiments of the present invention provide solutions for a TPM biosensor in which at least two molecular pairs are used, in which the two pairs have lifetimes that differ by at least a factor of three, at the physical and chemical conditions used in the biosensing system (e.g., at predetermined operational temperatures). Embodiments of the present invention enable the measurement of target with low concentrations while recording and analyzing a signal with a dynamic switching character that represents the target concentration. This enables the monitoring of target concentration over time.

FIG. 1A is a schematic diagram illustrating a technique for tethered particle motion biosensing, according to an embodiment of the invention. A surface 100 (e.g., substrate) on the interior of a cell has one end of a tether molecule 102 attached to it. The other end of the tether molecule 102 is attached to a particle 104, creating a primary bond between the particle 104 and surface 100. The tether 102 is flexible and allows the particle 104 to freely move within a region whose size depends on the length of the tether and whose location is centered on the point of attachment of the tether 102 to the surface 100.

Figure 1B:
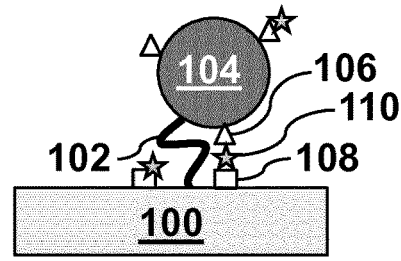

To enable biosensing, the particle 104 is functionalized with one or more capture molecules (e.g., ligands), such as capture molecule 106, and the surface 100 is functionalized with one or more capture molecules (e.g., ligands), such as capture molecule 108. Both capture molecules 106 and 108 are selected to have a binding affinity for a target substance 110. Moreover, capture molecules 106 and 108 are selected so that both can simultaneously bind to the target substance 110. This bound state is illustrated in FIG. 1B. When both capture molecules 106 and 108 are bound to target 110, it results in a secondary bond between the particle 104 and surface 100. As a result, the motion of particle 104 in this bound state is significantly constrained as compared to its motion in the unbound state shown in FIG. 1A. As a concrete example, a 1 μm diameter particle 104 is functionalized with oligo B as the capture molecule 106 and tethered to the substrate 100 with a 40 nm long double stranded DNA tether 102. The substrate 100 is functionalized with oligo A as capture molecule 108. The target molecule 110 is in solution or other matrix material introduced into a cell of the biosensor device. When the target is captured, the secondary bond constrains the motion of the particle. More generally, examples of capture molecules that may be used in embodiments of the invention include macromolecules, proteins, antibodies, antibody fragments, recombinant proteins, peptides, saccharides, polymers, molecularly imprinted polymers, polymers with coordination chemistry, nucleic acids, DNA, PNA, modified nucleic acids, aptamers, multivalent binders, small molecules, and combinations thereof Kinetics—Association and Dissociation Rates The reaction kinetics of the TPM biosensor described in FIG. 1A and FIG. 1B (as well as FIGS. 1C-H) is characterized by the association and dissociation rates between the target and each of the two capture molecules. In the following discussion, we will refer to the two capture molecules as A and B, and the target as T. We denote the association and dissociation rates of the interaction of T with A as $k^A_{on}$ and $k^A_{off}$, respectively. Similarly, we denote the association and dissociation rates of the interaction of T with B as $k^B_{on}$ and $k^B_{off}$, respectively. FIG. 2 is a schematic illustration of the four binding states of the capture molecules A and B with the target T, together with the corresponding association and dissociation rates between these states. When A and B are both simultaneously bound to T, the tethered particle is in a bound state. Otherwise, the tethered particle is in an unbound state. For each interaction (i.e., T with A and T with B) we also define association constants (i.e., affinities) $K^A_a = k^A_{on}/k^A_{off}$ and $K^B_a = k^B_{on}/k^B_{off}$, respectively, and dissociation constants $K^A_d = k^A_{off}/k^A_{on}$ and $K^B_d = k^B_{off}/k^B_{on}$, respectively.

All interactions are reversible, and it is conventionally assumed that the reaction rate constants are substantially equal for the interaction of the binding ligands A and B with the target T, and the complexes BT and AT, respectively. In other words, it is conventionally assumed that $k^A_{on} = k^B_{on}$ and $k^A_{off} = k^B_{off}$. In contrast, embodiments of the present invention do not make this assumption.

Among the two interactions, the one with the higher affinity (association constant $K_a$) controls the low-concentration regime in which the sensor is (most) sensitive. It also controls the response time of the sensor to changes in the concentration. In other words, the sensitive concentration regime is determined by interaction having the smaller dissociation constant $K_d$. The off-rate $k_{off}$ and on-rate $k_{on}$ of the interaction determine the response time to changes in the target molecule concentration. The off-rate $k_{off}$ determines the characteristic bond life time $\tau_{off} = 1/k_{off}$, which is important for the time-scale at which the system can respond to a decrease in the concentration of target molecules.

Among the two interactions, the interaction with the lower affinity (association constant $K_a$) controls the lifetime of the secondary bond. To increase statistics and measurement effectiveness, the binding time of the secondary bond should be kept short, but long enough to enable detection. For example, a secondary bond lifetime of the order of 0.01 second to 100 seconds is well-suited for detection.

Four characteristic times with distinct functions can be classified in two categories. In this example, the number of accessible binders on the particle and substrate are the same, only single bonds are assumed (no multiple bonds), and the binders on the particle are assumed to have a higher affinity than the binders on the substrate:

Two characteristic times relate to the characteristic times with which the biosensor responds to the change in target molecule concentration:

$\tau_{on}^{target}$ the characteristic time of the reaction with which target molecules attach to the binder on the particle side; This is the response time to increasing concentration of target molecules. The time $\tau_{on}^{target}$ depends on the target molecule concentration.

$\tau_{off}^{target}$ the characteristic time of the reaction with which target molecules detach from the binder on the particle side; This is the response time to a decreasing concentration of target molecules.

Both above-mentioned characteristic times depend on the reaction rate constants of the highest affinity binder with the target molecules, and the number of target molecules plays a role.

Two characteristic times relate to the generation of the state-switching signal:

$\tau_{on}^{secondary}$ characteristic time for the formation of a secondary bond. This time depends on the occupancy of the particle with the target molecule, and in that way on the concentration of target molecules. System parameters such as the diffusion rate of the particle, the positions of the binders, the tether length, the tether stiffness, and the molecular binding rate play a role in this time constant.

$\tau_{off}^{secondary}$ characteristic lifetime of the secondary bond. This depends mainly on the affinity of the weakest bond in the A-T-B complex.

In one embodiment of the TPM biosensor, the characteristic times $\tau_{on}^{target}$ and $\tau_{off}^{target}$ are kept below the relevant timescale $\tau_{matrix}$ over which the target molecule concentration changes inside the matrix wherein the target molecule is detected. For example, the time $\tau_{matrix}$ can be the timescale of a physiological process that is monitored by the biosensor. This ensures that the biosensor can respond timely to relevant changes in the target molecule concentration.

The characteristic time $\tau_{off}^{secondary}$ is preferably kept short to minimize sensor dead-time, but above the minimum time required for the detection ($T_{detection}$) of the motion state of particle. The secondary bond formation time $\tau_{on}^{secondary}$ is designed to be low to ensure good signal generation. Preferably, the secondary bond formation time has a lower limit: at the highest measurable concentration of target molecules [Target] the time required for formation of a secondary bond $\tau_{on}^{secondary}$ should not fall below $T_{detection}$ in order to ensure reliable discrimination between bound and unbound states.

Alternate TPM Embodiments

It will be appreciated that the principles of the present invention may be realized in various alternative embodiments. The embodiment of FIG. 1A and FIG. 1B uses a configuration where one type of capture molecule 106 is attached to the particle 104 and another type of capture molecule 108 is attached to the surface 100. Essentially the same functionality may be implemented using embodiments where one or both of the capture molecules are attached to the tether 102 instead.

Figure 1C:
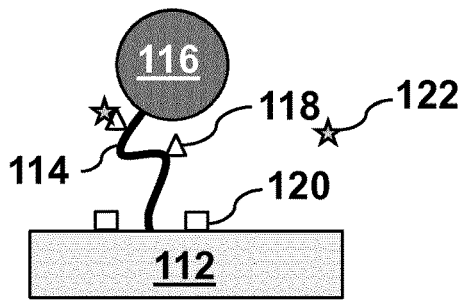
FIG. 1C and FIG. 1D are schematic diagrams illustrating a tethered particle biosensing configuration in an unbound state and bound state, where the tether and substrate are functionalized with capture molecules, according to an embodiment of the invention.
Figure 1D:
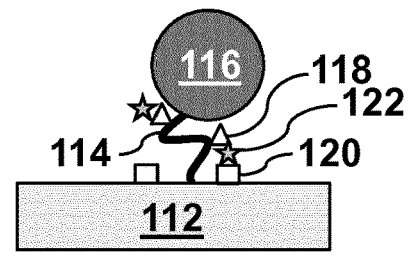
Figure 2:
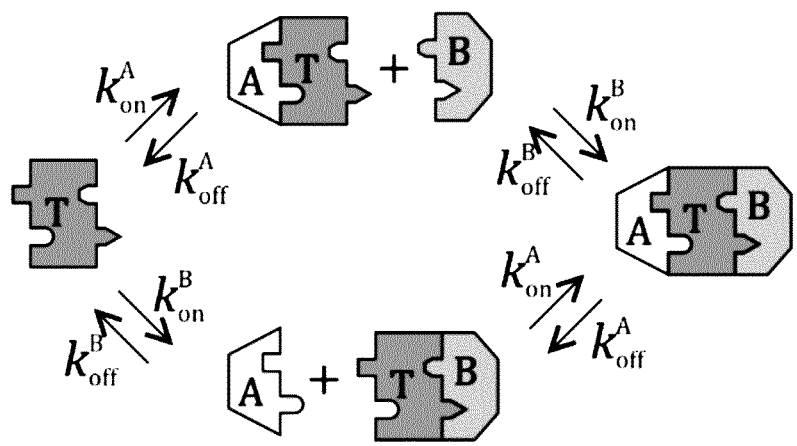
FIG. 2 is a schematic diagram illustrating four different binding states of two capture molecules A and B with a target T, together with the corresponding association and dissociation rates between these states, according to an embodiment of the invention.

For example, the embodiment of FIG. 1C and FIG. 1D uses a configuration where one type of capture molecule 118 is attached to the tether 114 instead of to the particle 116, and another type of capture molecule 120 is attached to the surface 112. When both capture molecules 118 and 120 bind to the target substance 122, the motion of particle 116 is constrained, just as in the embodiment of FIG. 1A and FIG. 1B.

Figure 1E:
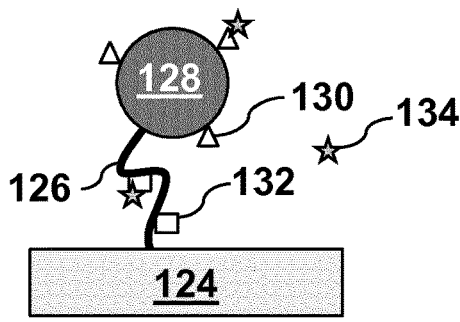
FIG. 1E and FIG. 1F are schematic diagrams illustrating a tethered particle biosensing configuration in an unbound state and bound state, where the particle and tether are functionalized with capture molecules, according to an embodiment of the invention.
Figure 1F:
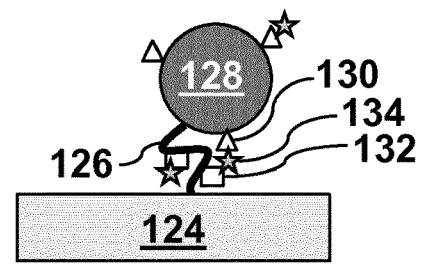

The embodiment of FIG. 1E and FIG. 1F uses a configuration where one type of capture molecule 132 is attached to the tether 126 instead of to the surface 124, and another type of capture molecule 130 is attached to the particle 128. Again, when both capture molecules 130 and 132 bind to the target substance 134, the motion of particle 128 is constrained.

Figure 1G:
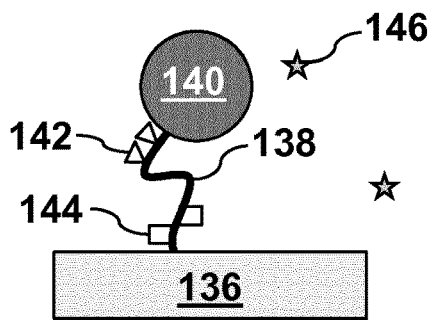
FIG. 1G and FIG. 1H are schematic diagrams illustrating a tethered particle biosensing configuration in an unbound state and bound state, where the tether is functionalized in two locations with capture molecules, according to an embodiment of the invention.
Figure 1H:
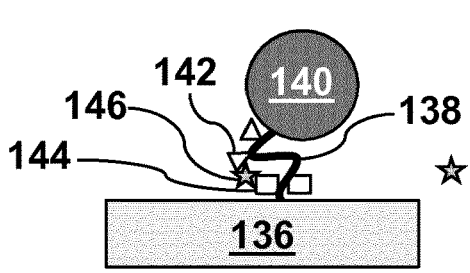

The embodiment of FIG. 1G and FIG. 1H uses a configuration where one type of capture molecule 142 is attached to the tether 138 instead of to the particle 140, and another type of capture molecule 144 is attached to the tether 138 instead of to the surface 136. Again, when both capture molecules 142 and 144 bind to the target substance 146, the motion of particle 140 is constrained.

It will also be appreciated that in these embodiments the capture molecules of type A and type B can be interchanged or reversed to achieve a functionally equivalent biosensor.

Figure 3A:
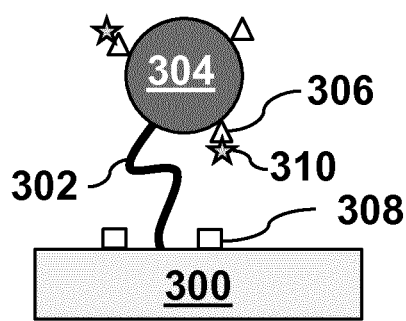
FIG. 3A and FIG. 3B are schematic diagrams illustrating a tethered particle biosensing configuration in an unbound state and bound state, where the particle and substrate are functionalized with a capture molecule and target analogue to implement a competitive assay, according to an embodiment of the invention.
Figure 3B:
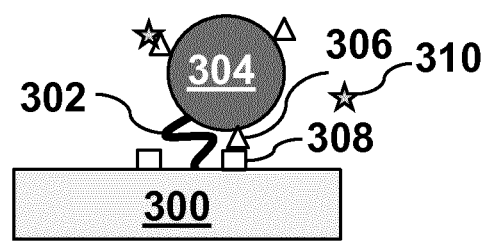

Biosensors implementing the principles of the present invention may also be implemented in competitive assay configuration. For example, FIG. 3A and FIG. 3B show again a particle 304 attached to a surface 300 by a tether 302. In this configuration a capture molecule 306 is attached to the particle 304 but a target analogue 308 instead of another capture molecule is attached to the surface 300. In this case, the target analogue 308 and target substance 310 both compete to bind to capture molecule 306. When the target substance 310 is present and binds to the capture molecule 306, it prevents the target-analogue 308 from binding to that capture molecule 306. Consequently, the particle 304 is less likely to have a constrained motion in the presence of the target.

It will be appreciated that substantially the same functionality is obtained if the target analogue is attached to the particle and the capture molecule is attached to the surface. Thus, another embodiment is obtained by reversing their roles. In addition, substantially the same functionality is obtained if the target analogue and/or capture molecule is attached to the tether instead of to the particle or surface.

To have high measurement statistics, the binding between target-analogue and capture molecule is preferably selected to be short-lived (high dissociation rate); this can be tuned by the design and selection of the target-analogue, its conjugation method, etc. For sensing the target at low concentrations, the binding between target and capture molecule is selected to be long-lived (low dissociation rate); this can be tuned by the design and selection of the capture molecule, its conjugation method, etc.

Motion Analysis Method

In a TPM biosensor, the pattern of motion of the tethered particle depends upon whether the particle is in a bound or unbound state. Thus, the state of the particle can be inferred by measuring the particle motion, e.g., coordinate parameters such as the coordinate positions in the x-y plane parallel to the surface. For example, FIG. 4A illustrates a tethered particle in an unbound state and FIG. 4C illustrates a tethered particle in a bound state where its motion is restricted. The measured x-y coordinate positions of the unbound particle over time are shown as individual dots in the image of FIG. 4B and the measured x-y coordinate positions of the bound particle over time are shown as individual dots in the image of FIG. 4D. An important part of a TPM biosensor is the measurement of these positions (or other coordinate parameters) over time, and the analysis of these measurements to identify the binding state of the particle and the concentration of the target substance. For example, in one known technique, a rotational symmetry parameter of the motion is calculated from an eigendecomposition of the covariance matrix of the x-y coordinate position data. Because the distribution of points in FIG. 4B is symmetrical, while the distribution in FIG. 4D is not, this symmetry parameter can be used to distinguish between bound and unbound particle states. Other parameters may also be useful in TPM, such as the mean squared displacement, motion amplitude, and step size. Histograms of the motion parameters (e.g., coordinate and step-size as function of time) are conventionally used to discriminate between the different states. Distinct states can be identified by applying thresholds to the motion parameters to categorize the data. The thresholds are chosen based on the expected signal from the system. However, many conventional data analysis methods are ineffective in the analysis of particle motion in heterogeneous systems. In these heterogeneous systems both the number of binding states, and the position and size of the bound states vary from particle to particle. Heterogeneous systems arise often in biochemical assays due to the stochastic nature of the reactions.

The particle/molecules/substrate system can be in various states, because the number, location and orientation of the bonds are influenced by stochastic/random binding reactions. The number of distinct states increases when there are multiple types of capture molecules whose interactions with the target substance have different kinetics. This heterogeneity leads to a challenge in the analysis of the data, as the moment and the type of change in the particle motion are not a priori known. Furthermore, the particles can interact with the substrate also by other various interactions, e.g., non-specific interactions. Therefore, a sensitive and robust analysis method that is able to detect the heterogeneous binding states should be used in order to achieve a good sensitivity and specificity of the biosensing technology.

Embodiments of the present invention provide a data analysis method and an algorithm for the detection of changes in a system with heterogeneous mobility states, which may be used to analyze the mobility changes observed in the tethered particle biosensor system. The data analysis method encompasses a powerful technique for detecting the moment of significant changes in the distribution of data in a continuous stream of data. This method is then implemented in a technique for the detection of changes in particle motion.

Embodiments of this invention analyzes the motion data of a tethered particle, with the aim to detect statistically significant changes in the state of the tethered particle system. These changes include the occurrence of specific secondary bonds and non-specific secondary bonds.

Accordingly, embodiments of the invention preferably include a combined analysis of more than one data channel. This increases the robustness of state change determination. Embodiments preferably also include analysis of a divergence function. This gives an accurate determination of the state change and the time of the state change.

Specifically, multiple spatial coordinate parameters are measured over time, producing multiple corresponding data channels. These channels are individually analyzed, and then the information from the analysis of the different channels is combined to give reliable and robust indications of the particle state changes. In one implementation, for example, eight channels representing eight spatial coordinate parameters are used: two Cartesian coordinates, their two time derivatives, two polar coordinates, and their two time derivatives. It is noted that a spatial coordinate parameter herein refers to position coordinates and parameters derived from them such as motion range, mobility, position range, velocity, angle range, step size, or other derived parameter. The coordinate parameter may also relate to a change of distance and/or relative orientation. The coordinate parameter may also be a derived parameter such as time derivative or second moment.

In an embodiment, the analysis of the coordinate channels includes using a second moment divergence function. This allows for two key determinations: 1) quantification of the significance of an observed deviation in a data channel and 2) determination of the divergence point (i.e. a time point) at which the behavior of the particle has changed, through back-extrapolation of the second moment divergence function.

Observed changes in a single data channel are correlated with other data channels. If the observed change matches predetermined significance thresholds, a change in particle state is detected.

In an embodiment, the data analysis method is based on continuous detection of changes in the second moment of the data at arbitrary significance levels. In the first step, the analysis algorithm uses the second moment divergence function to detect the changes in motion and determine the time-point of the change. In the second step, time intervals with similar motion data are combined using the Kolmogorov-Smirnov test. In the final step, the area covered by the motion and the step-size is used to weed out false-positive detections of events.

The motion data of the tethered particles is represented by the particle position and the step sizes as a function of time. The second moment divergence function $C(n)=\Sigma_{i=1,n}(x_i-\mu)^2-\sigma^2$ quantifies the deviation of a series of data points $x_i$ from a distribution with a certain standard deviation $\sigma$ and average $\mu$. The second moment divergence function $C(n)$ is calculated up to data point n at a time $t_n$. For TPM data this reflects the motion data up to that point in time. We assume that the data is sequential, with the sequence determined by the time of the measurement and that the data points are taken at equidistant time points. For data in which the mean $\mu$ and standard deviation $\sigma$ of the position values do not change, $C(n)$ is going to fluctuate around $\langle C(n) \rangle = 0$. If the distribution changes, $C(n)$ will deviate from zero, signifying that the state of the particle has changed.

If the distribution of the data differs from the reference parameters $\mu$ and $\sigma$, $C(n)$ will increase linearly with a slope $S=\langle (x_i-\mu)^2-\sigma^2 \rangle$. By performing a linear fit to the part of $C(n)$ that starts diverging from zero the increase in $C(n)$ can be determined. By back-extrapolating the fit it is possible to estimate the point $t_d=-a/b$ at which the divergence started. Care has to be taken to only include data points that are part of the rising/declining flank of $C(n)$ in the fit, and that enough data points are included to average out the random fluctuations.

The detection algorithm detects significant changes in the motion of the particles. In step 1, the center of the motion pattern is determined as reference point and the motion is represented in Cartesian and polar coordinates, and the corresponding step sizes in each of these coordinates calculated. The data in each of these channels is scanned for significant changes in motion behavior, based on the second moment divergence function, and the results of all 8 channels are combined using criteria that combine detected deviations in all 8 channels. At the end of the first step of the algorithm all data has been parsed, and a list of candidate events has been constructed. In the next step of the algorithm these candidate events are scrutinized further.

In step 2, the data between the detected events are compared using the Kolmogorov-Smirnov test in several passes, in which the required significance of the test is incremented. The list of significance levels used for the progressive passes is first $0.1\sigma$, and then increases from $0.5\sigma$ up to $3\sigma$ in steps of 0.25. Events are removed and intervals are combined when no significant difference is found.

In step 3, the physical motion parameters of the particles are determined and intervals with no clear change in behavior are removed.

Embodiments of the invention enable the use of a TPM biosensor for measuring the concentration of target molecules in a matrix over time. By using capture molecules having two distinct affinities for the target molecule, the sensitivity range and response time of the biosensor and the detection rate are optimized separately. Preferably, the dissociation rates of the capture molecules with respect to the target substance differ by at least a factor of three, at the physical and chemical conditions used in the biosensing system. The off-rate constant $k_{off}$ of an oligo interaction can be estimated using the semi-empirical relationship $k_{off}=10^{3-0.5n}$ where n is the number of complementary consecutive nucleotides at room temperature in PBS buffer. Thus, by selecting n appropriately, the off-rate can be selected. For example, if Oligo B has 11 nucleotides complementary to the target molecule, this yields an estimated $k_{off}=0.003$ $s^{-1}$, which corresponds to a characteristic binding time $\tau_{off}=1/k_{off}$ of 5 minutes. If Oligo A has 8 complementary nucleotides, which has an expected $k_{off}=0.1$ $s^{-1}$. This corresponds to a characteristic bond lifetime $\tau_{off}=1/k_{off}$ of 10 seconds.

These techniques increase the sensitivity and specificity of the TPM biosensor by enabling a better recognition of different states and by enabling identification of transition events between states.

The signal processing of the channels may separately detect individual switching events of single particles. Alternatively, it may detect switching of an ensemble of particles, e.g. the average number of switching events per unit time. The sensing of a target substance can also be performed by counting an average number of bound particles or by recording the average time of being in the bound state.

For the example of a sandwich-type biosensor with short-lived secondary bonds, the event detection is typically sensitive at lower concentrations than counting of bound particles or recording the average time in bound state. At higher target concentrations, the detection of events may saturate and be less sensitive, while counting of bound particles or recording the average time in bound state may be sensitive.

Therefore, it can be useful to combine the different detection methods in a biosensing system, so that stitching of dose-response curves can be performed, for higher reliability, higher dynamic range of detection, and higher precision.

Device

In one embodiment, the present invention provides an optical biosensing device for implementing the techniques described above.

As shown in FIG. 5, the device includes a light source 500 that emits light for electromagnetic excitation of tethered particles. The excitation light 508 enters a liquid cell 502 that has on its interior a biosensing surface with tethered particles, as described in detail above. As a result of the interaction of the excitation light 508 with the tethered particles, light 510 is exits the cell 502 and is sensed by an imaging detector 504. For a high signal to noise ratio, the preferred imaging method is dark-field imaging, e.g. the light emitted from the particles (e.g. scattering, fluorescence, luminescence, phosphorescence) is measured against a dark background. Tethered particle coordinate parameters may be measured directly, e.g. via spatial coordinates measured from an image of emitted light. For example, in one implementation, the particle motion was measured using a Nikon Ti-E inverted microscope (Nikon Instruments Europe BV, The Netherlands), at a total magnification of 20× using an iXon Ultra 897 (Andor, Belfast, UK). The particle motion in a field of view of 405×405 µm² was recorded for 5 minutes at a frame rate of 30 Hz under dark field illumination conditions.

Imaging signals are processed and analyzed in a processor/analyzer 506, which determines particle switching events and target substance concentration.

In alternative embodiment, the particles can be excited using a voltage source instead of a light source. The excitation pathway is designed to mainly excite the particles and to avoid that light otherwise generated reaches the imaging detector. Optical excitation methods can include, for example, total internal reflection (TIR) excitation or high angle (HA) illumination.

In alternative embodiments, tethered particle coordinate parameters may be determined indirectly, e.g., via a spectroscopic change or a color change that relates to a spatial coordinate, for example in the case of plasmonic sensing with a change of plasmonic resonance.

For tuning purposes, one can integrate a moving component in the system, e.g., a substrate or a lens or an imaging sensor mounted on a linear stage. The motion of the component along the optical axis allows for the tuning of the focal plane with respect to the sensor plane, helping to form a sharp image of the object and its emitted light. Actuation systems can be used such as e.g. a voice-coil-motor (VCM) or silicon MEMS.

In operation, the device performs continuous monitoring with single molecule resolution, determining e.g., the concentration of a DNA target as a function of time. Micrometer sized particles are tethered in close proximity to the sensor surface by a short (40 nm) primary dsDNA tether. The particles and the substrate have each been functionalized with ssDNA oligos, both complementary to a different part of the DNA target. In presence of the target one or both oligo can bind to the target molecule simultaneously; the particle then becomes bound to the surface with a secondary bond. This results in a clear change in the motion of the particle compared to the motion of a particle that is tethered with only the primary tether. The frequency or activity of binding and unbinding events of the secondary bond is a direct measure for the concentration of the target in solution. Furthermore, the target solution can be exchanged without the need to regenerate the system, as the tethered particle forms a self-contained system. The secondary bond that forms via the target molecule is designed to be reversible; the interaction between the DNA target and both oligos is deliberately designed to be weak such that the formed bond is reversible. This allows the system to respond to both increasing and decreasing target concentrations and is therefore suitable for the continuous monitoring of the concentration of target molecules. The dissociation rates of the two interactions, however, preferably differ by a factor of three or more.

Tracking of the particle motion is performed by determining the center-of-intensity of the bright particle on the dark background. Trajectory analysis was performed on the trajectories of many individual particles to detect and quantify the number of occurrences and duration of the binding and unbinding events during the measurement. To achieve this, the algorithm scans through the motion data, detecting significant changes in the distribution of the particles position in the motion data. These changes correspond to the formation or breaking of a secondary interaction. The detection algorithm is capable of detecting binding events of a single particle at multiple locations; secondary bonds can form on any location where the particle comes within the distance required to make a secondary bond to the substrate and both the particle and substrate have the oligos required for bond formation. During the functionalization reactions, the antibodies and oligos are randomly distributed on the substrate and the particle surface. Potential binding spots are thus heterogeneously distributed on the surface. All measurement data is analyzed with the same algorithm, ensuring that the all detected events satisfy the same criteria for detection. The sensitivity for the detection of particle mobility changes with a duration longer than 0.8 seconds is over 80%.

The shape of the motion pattern of a tethered particle is interpreted in terms of the motion amplitude and the symmetry of the motion. From the motion pattern of each particle the amplitude of the major ($A_{major}$) and minor ($A_{minor}$) axis of motion was determined by calculating the covariance matrix of the position data. From the motion amplitudes the symmetry parameter $S_{sym}=A_{minor}/A_{major}$ is calculated. The radial confinement parameter is defined as $Rc=\sigma_r/\bar{r}$ and used to exclude particles with a confined ring-shaped motion pattern.

Supplemental details regarding embodiments of the invention are included in the priority application, U.S. 62/439,833 filed 28 Dec. 2016, which is incorporated herein by reference.

The invention claimed is:

1. A method for biosensing a target substance, the method comprising:
bringing a solution or other matrix material containing the target substance into contact with a sensor device having a surface, a collection of particles tethered to the surface by tether molecules, and a collection of capture molecules,
wherein the collection of capture molecules comprises first capture molecules (CM1) attached to the particles or to the tether molecules, and second capture molecules (CM2) attached to the surface or to the tether molecules,
wherein the CM1 are selected to bind to the target substance and have a first target dissociation rate, and the CM2 are selected to bind to the target substance and have a second target dissociation rate that differs from the first target dissociation rate by at least a factor of three;
detecting a time series of a spatial coordinate parameter of the particles, wherein the spatial coordinate parameter is measured relative to the surface,
identifying within the detected time series a time sequence of individual association/dissociation events of the target substance with the capture molecules, wherein each of the events corresponds to a change between binding states of the CM1 and the CM2 to the target substance;
determining a concentration of the target substance in the solution or other matrix material from the identified time sequence of individual association/dissociation events.

2. The method of claim 1 wherein the change between binding states is a change between a sandwich-like state wherein the target substance is bound to and sandwiched between both CM1 and CM2 and an open state wherein the target substance not bound to CM1, said target substance not bound to CM2 or the target substance not bound to both CM1 and CM2.

3. The method of claim 1 wherein determining a concentration of the target substance from the detected time sequence of individual association/dissociation events comprises determining characteristic times of reactions of the capture molecules with the target sub stance.

4. The method of claim 1 wherein determining a concentration of the target substance from the detected time sequence of individual association/dissociation events comprises analyzing the spatial coordinate parameter and a second moment divergence of the spatial coordinate parameter.

5. The method of claim 1 wherein detecting a time sequence of individual association/dissociation events of the target substance with the capture molecules comprises measuring multiple spatial coordinate parameters of the particles and second moment divergences of the multiple spatial coordinate parameters of the particles.

6. The method of claim 1 wherein determining a concentration of the target substance from the detected time sequence of individual association/dissociation events comprises analyzing the measured spatial coordinate parameter and/or its time derivative with a second moment divergence function to determine the significance of an observed deviation in a data channel and to determine the divergence time point at which the behavior of the particle has changed, through back-extrapolation of the second moment divergence function.

7. The method of claim 1 wherein determining a concentration of the target substance from the detected time sequence of individual association/dissociation events comprises determining a duration of target substance capture states or an average occupancy of the capture molecules by the target substance.

* * * * *

UNITED STATES PATENT AND TRADEMARK OFFICE
CERTIFICATE OF CORRECTION

PATENT NO. : 11,703,503 B2  Page 1 of 1
APPLICATION NO. : 16/471113
DATED : July 18, 2023
INVENTOR(S) : Emilius Willem Adriaan Visser, Leonardus Josephus van Ijzendoorn and Menno Willem José Prins It is certified that error appears in the above-identified patent and that said Letters Patent is hereby corrected as shown below:

In the Claims

Claim 3, Column 14, Line 19 reads:
"capture molecules with the target sub stance."
Whereas it should read:
"capture molecules with the target substance."

Signed and Sealed this
Twenty-eighth Day of November, 2023

Katherine Kelly Vidal
*Director of the United States Patent and Trademark Office*